United States Patent [19]
Kuo

[11] Patent Number: 5,547,721
[45] Date of Patent: Aug. 20, 1996

[54] FLOWER VASE

[76] Inventor: Hsin H. Kuo, P.O. Box 368, Alhambra, Calif. 91802

[21] Appl. No.: 175,649

[22] Filed: Dec. 30, 1993

[51] Int. Cl.$^6$ ................................................. A47G 7/06
[52] U.S. Cl. ..................... 428/34.1; 47/41.01; 428/905
[58] Field of Search .................... 428/34.1, 15, 905; 47/41.01

[56] References Cited

U.S. PATENT DOCUMENTS

| | | | |
|---|---|---|---|
| 1,579,305 | 4/1926 | Goldberg | 47/41.13 X |
| 1,694,214 | 12/1928 | Ginder | 47/41.01 X |
| 2,807,901 | 10/1957 | Gilowitz | 428/13 X |
| 3,400,890 | 12/1966 | Gould | 428/26 X |
| 4,165,835 | 8/1979 | Dearling | 47/41.01 X |
| 5,217,696 | 6/1993 | Wolverton et al. | 47/48.5 X |

*Primary Examiner*—Henry F. Epstein

[57] ABSTRACT

According to the present invention, a vase is set forth which includes a container to define a first space to receive either live or imitation plant. The container has a closed base. A housing as defined in the container to define a second space separate from the first space, the housing has an opening at the base. At least one of (a) a light or (b) a scent chemical and blower are disposed in the housing. When the light is energized, the light is adapted to illuminate through said opening to provide area lighting at the base of the vase. When the scent chemical and blower are used and the blower is energized, scented air is driven from the housing second space to provide proximal air freshening.

5 Claims, 2 Drawing Sheets

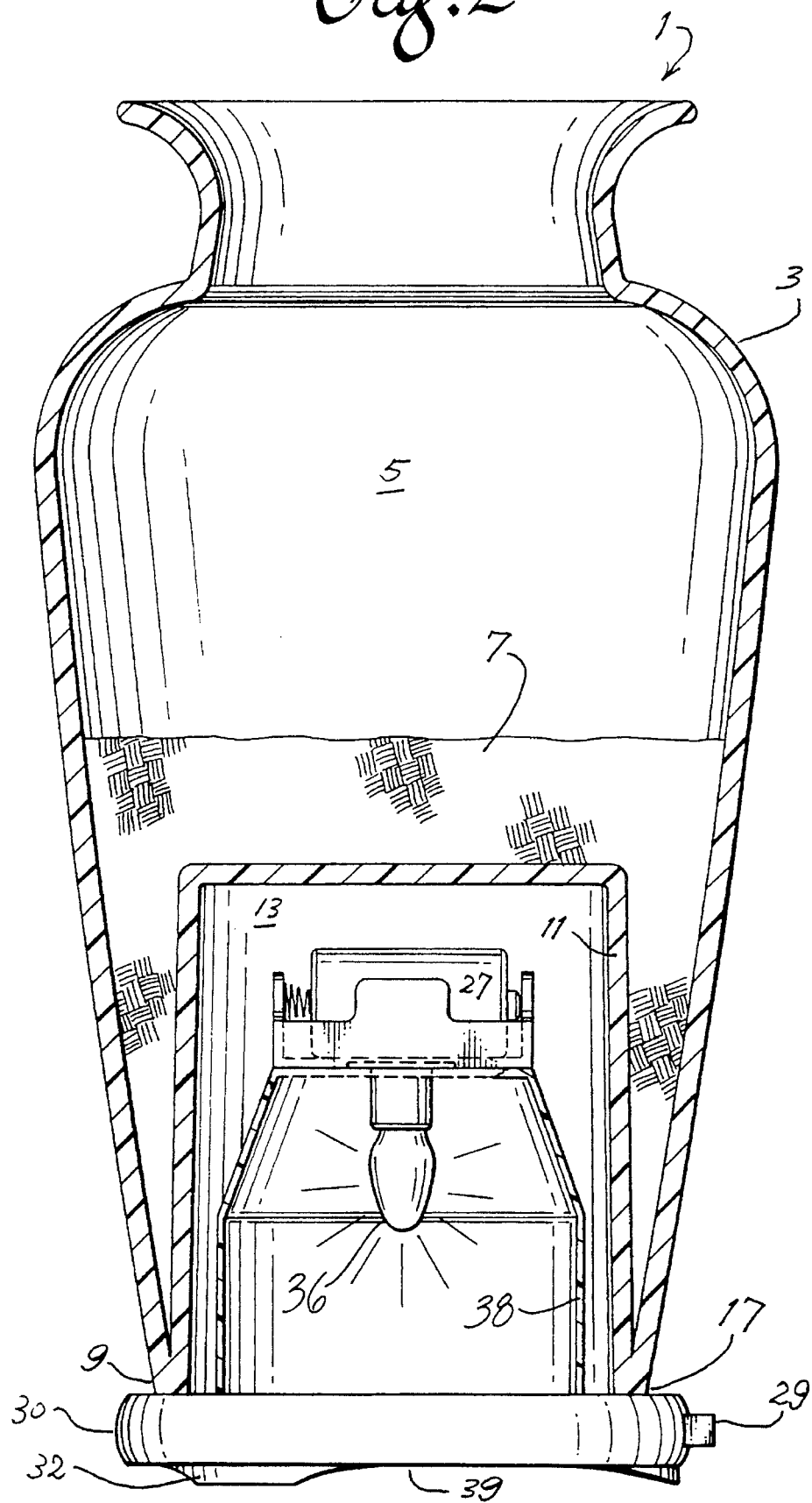

FLOWER VASE

FIELD OF THE INVENTION

The present invention relates to vases for plants, both live and imitation.

BACKGROUND

It is well known in the prior art to provide vases for plants, both live and imitation. These vases are adapted to provide a visual, decorative benefit within at the home or office.

It is also known to provide a fan, the horizontal diffuser of which is fashioned into a conical cavity to receive a plant as described in U.S. Pat. No. 1,694,214 issued Aug. 25, 1927 to Ginder. It is also known to provide a light, vase and air purification device as described in U.S. Pat. No. 5,217,696 issued Jan. 8, 1993 to Wolverton, et al.

However, it is unknown to me to provide a vase, adapted to hold either a live or imitation plant, in combination with a method for providing for proximity air freshener, accent lighting, or both.

SUMMARY

Accordingly, I set forth a vase having generally a container defining a first space adapted to receive a plant either live or imitation. At the bottom of the container is a closed base to prevent, in the event that a live plant is used, soil and water from leaking from the first space.

Defined in the container is a housing which creates a second space separate from the first space. The housing is impermeable to water to prevent soil moisture, should a live plant be used, from intruding into the housing second space. The housing opens to the base of the container. As an example, and not by way of limitation, the housing may be cylindrical, the cylindrical walls of which terminate at the base.

Disposed in the housing are at least one of a light or scent generating means. The light is adapted to illuminate from the housing out of the opening in the base to create a decorative as well as a general over-all illumination effect. The scent generating means include a blower to drive the scent from the opening to the area proximate the base to create an air freshening, and scenting effect. The scent generating means may include a scent generating chemical or cake along with a small electric fan adapted to drive the scent from the cake through the opening for the desired effect.

To power the selective light and/or blower, means are provided for powering the light or blower. The powering means may be by way of batteries disposed in the housing or may be an external cord adapted to be connected to an external power source such as an external power system. To selectively energize the light or blower, a switch is provided.

Accordingly, it can be understood that the vase according to my invention not only provides the decorative effect heretofore found in vases holding either live or imitation plants, but also provides an additional benefit of illumination and/or proximal air freshening and air scenting.

BRIEF DESCRIPTION OF THE DRAWINGS

These and other features and advantages will become better understood with reference to the specification, claims and drawings in which:

FIG. 2 is a section view of yet another embodiment of the present invention,

SPECIFICATION

Figure 1:
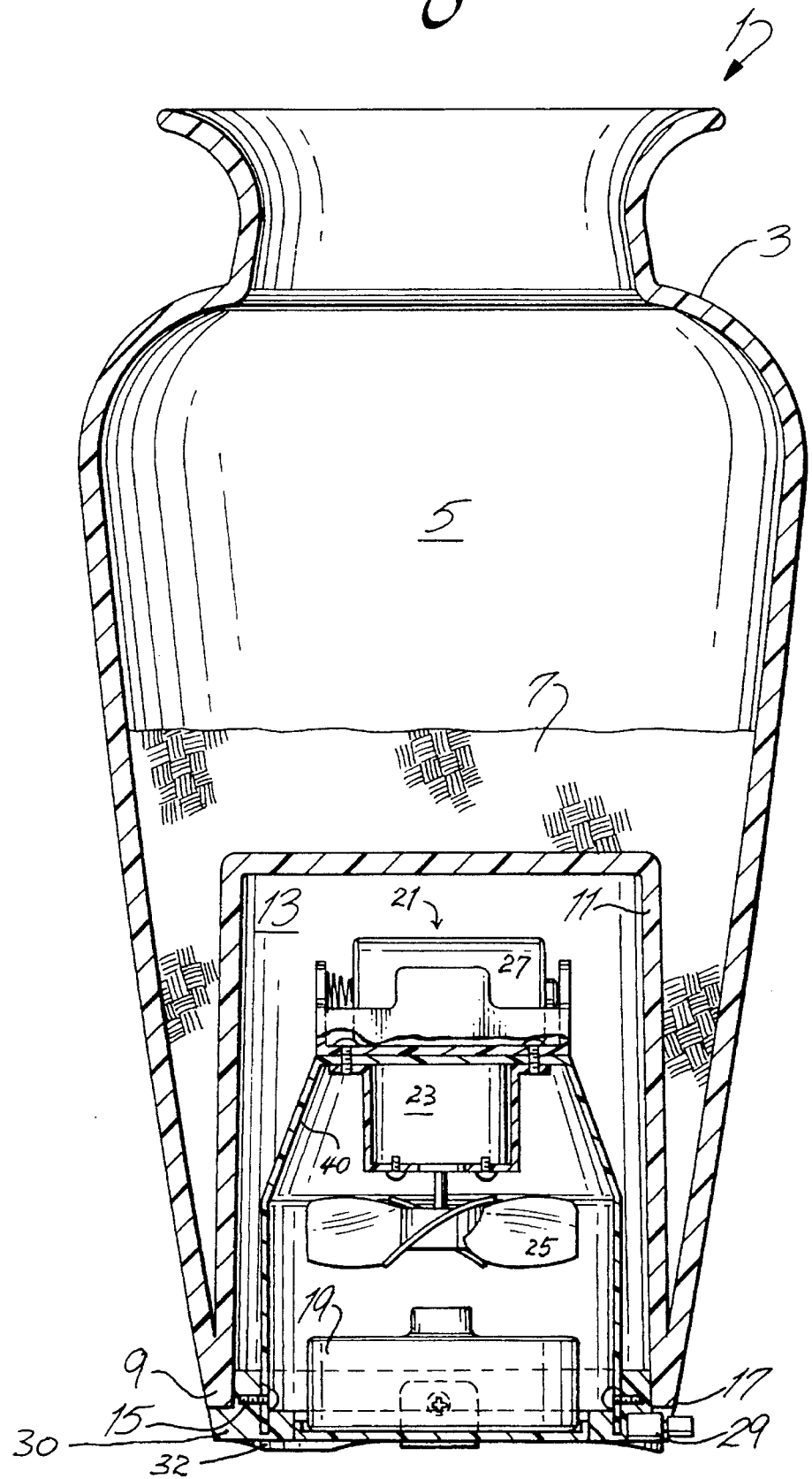
FIG. 1 is a section view of a vase according to one embodiment of the present invention.

With reference to the drawings, FIG. 1 shows one embodiment of my invention.

A vase 1, shown here generally as a traditional, conical, fluted style but may be of any design, includes a container 3 defining a first space 5 adapted to receive either a live plant or an imitation plant. To accommodate a live plant, the container 3 may be of plastic, porcelain or clay design and is impermeable to water so as to retain soil moisture. Soil 7 is shown in the drawing to accommodate a live plant. It is to be understood that when an imitation plant is selected, soil 7 may be replaced with marbles or any suitable mechanism to retain the imitation plant. The upstanding vase 1 terminates at its lower extremity at a base 9 which provides upstanding support for the vase 1.

In the container 3 is a housing 11 defining a second space 13 separate and apart from first space 13 5. To accommodate a live plant, and soil 7 and its attendant moisture to sustain the live plant, housing 11 is impermeable to water to prevent moisture from intruding into second space 13. Housing 11 is open to the environment at its lower end to define an opening 15 generally at base 9. As can be seen in the drawings, where container 3 at at least its lower portions has a generally downwardly narrowing conical shape, the housing 11 at opening 15 merges with the shape of container 3 to define a circular rim 17. Of course, it is to be understood that other shapes of the container 3 and housing 11 could also be used without it departing from the spirit or scope of my invention.

Disposed in housing space 13 is a means for generating a scent such as, for example, a chemical either in liquid, solid or gel form retained, as shown on the drawings, in a canister 19 disposed proximate opening 15. In a well known fashion, a scent is emitted from canister 19 into housing second space 13.

To effectively drive the scent emitted from canister 19 from second space 13, a blower 21 is also provided in housing 11. Preferably blower 21 is disposed to forcefully ventilate housing second space 13 over canister 19 and from opening 15 at container base 9. Blower 21 includes a motor 23 driving an impeller 25 for the desired effect. Means are provided for energizing the blower motor 23 as by one or more batteries 27 or, in the alternative, motor 23 may be driven by an external power source such as by an electrical cord connected to external power. Blower 21 and its batteries 27 are supported in the space 13 by a support 40. A switch 29 provides for selectively energizing motor 23 to turn the blower 21 on and off.

Housing second space 13 communicates with the outside environment as by any suitable means. For example, bores (not shown) may be provided in container 3 to communicate with the housing second space 13 at rim 17. Alternatively, and as shown in FIG. 1, container 3 may be set in a stand 30 which spaces rim 17 above the floor or table supporting the vase 1. Stand 30 has a plurality of legs 32 defining passages 34 there between through which the scented air is driven from housing second space by blower 21.

As can be appreciated the vase 1 according to this embodiment of the present invention not only provides for the visually pleasing effect of a vase and plant arrangement as heretofore known, but also contains a further advantage of providing for air scenting and freshening in the area proximate to vase 1 to pleasingly affect the sense of smell.

With reference to FIG. 2 a further embodiment of the present invention is shown. Like components are referred to by like reference numbers.

Disposed in housing second space 13 are illuminating means embodied as a light 36. Light 36 may be of any desired color and is disposed to direct its illumination toward opening 15. Accordingly the light 36 may be supported above opening 15 by a reflector 38. Means are provided for powering the light 36 as by batteries 27 or an external power source. A switch 29 provides for a selectively energizing light 36.

The light generated is directed, as stated above, to opening 15. The light is directed to outside container 3 as by bores in the container at rim 17 or by, as described above, providing a stand 30 to raise opening 15 above the floor supporting vase 1. Accordingly, light emanating from housing second space is directed through passages 34 to provide the desired illuminating effect. It is to be understood that a suitable colored light may be selected to coordinate with the color of vase 1 or to provide general illuminating or as a night light.

While I have described a first and second embodiment of my invention, it is to be understood that the vase could combine the desired effects of both illumination and air freshening by disposing the light, blower and scent canister in the housing.

It is to be understood that many modifications, reconfigurations or other changes may be made to the vase accordingly to my invention without departing from the spirit and scope of the claims hereinafter set forth.

What is claimed is:

1. A vase comprising:
   a container defining a first space to receive a plant, said container having a substantially closed base;
   a housing defined in said container to define a second space separate from the first space, said housing having an opening at and through said base;
   at least one of
   (a) a light adapted to illuminate through said opening, or
   (b) means for generating a scent and a blower to drive the scent from the scent generating means through the opening disposed in said base; and
   means for powering said light or blower.

2. A vase comprising:
   a container defining a first space to receive a plant, said container having a substantially closed base;
   a housing defined in said container to define a second space separate from the first space, said housing having an opening at and through said base;
   means for generating a scent and a blower to drive the scent disposed in said housing from said scent generating means through said opening; and
   means for selectively powering said blower to drive out the scent.

3. A vase as set forth in claim 2 wherein said housing opening and said base are coterminus, said vase further including a stand to raise said opening, said stand having a plurality of legs defining passages through which the scent is driven by said blower.

4. A vase comprising:
   a container defining a first space to receive a plant, said container having a substantially closed base;
   a housing defined in said container to define a second space separate from the first space, said housing having an opening at and through said base;
   a light disposed in the housing and adapted to illuminate through said opening; and
   means for selectively energizing said light.

5. The vase as set forth in claim 4 wherein said housing opening and said base are coterminus, the vase further including a stand to elevate said housing opening, said stand including a plurality of legs defining passages through which the light illuminated through said opening passes to illuminate the area surrounding the vase.

* * * * *